(12) United States Patent
Yoshinaga et al.

(10) Patent No.: US 11,931,006 B2
(45) Date of Patent: Mar. 19, 2024

(54) BENDING OPERATION MECHANISM OF ENDOSCOPE, AND ENDOSCOPE

(71) Applicant: OLYMPUS CORPORATION, Tokyo (JP)

(72) Inventors: Takuto Yoshinaga, Hino (JP); Tsukasa Ota, Hachioji (JP); Xiongwei Wang, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 665 days.

(21) Appl. No.: 17/095,927

(22) Filed: Nov. 12, 2020

(65) Prior Publication Data

US 2021/0113064 A1 Apr. 22, 2021

Related U.S. Application Data

(63) Continuation of application No. PCT/JP2019/006816, filed on Feb. 22, 2019.

(30) Foreign Application Priority Data

May 14, 2018 (JP) .................. 2018-093035

(51) Int. Cl.
*A61B 1/00* (2006.01)
*A61B 1/005* (2006.01)

(52) U.S. Cl.
CPC .......... *A61B 1/0057* (2013.01); *A61B 1/0052* (2013.01)

(58) Field of Classification Search
CPC ..... A61B 1/0057; A61B 1/0052; A61B 1/005; A61B 1/0056; A61B 1/00; A61B 1/00066
USPC ......................................... 600/146, 149, 148
See application file for complete search history.

(56) References Cited

U.S. PATENT DOCUMENTS 4,688,555 A * 8/1987 Wardle ............... A61B 1/00042
600/149

FOREIGN PATENT DOCUMENTS

| EP | 0165718 A2 | 12/1985 |
| JP | S59-73901 U | 5/1984 |
| JP | S61-50545 A | 3/1986 |
| JP | S63-242217 A | 10/1988 |
| JP | 2005-218569 A | 8/2005 |

(Continued)

OTHER PUBLICATIONS

International Search Report dated May 28, 2019 issued in PCT/JP2019/006816.

*Primary Examiner* — Timothy J Neal
*Assistant Examiner* — James Edward Boice
(74) *Attorney, Agent, or Firm* — Scully, Scott, Murphy & Presser, P.C.

(57) ABSTRACT

A bending operation mechanism of an endoscope including: a first pulley configured to pull a first wire by being rotated in a first rotation direction; a second pulley, which is coaxial with the first pulley, configured to pull a second wire by being rotated in a second rotation direction opposite to the first rotation direction; and a rotation shaft member including a first protrusion that engages only with the first engagement portion of the first pulley when the rotation shaft member is rotated in the first rotation direction from a neutral position when a bending portion is not bent and a second protrusion that engages only with the second engagement portion of the second pulley when the rotation shaft member is rotated in the second rotation direction from the neutral position.

20 Claims, 12 Drawing Sheets

(56) References Cited

FOREIGN PATENT DOCUMENTS

| JP | 2005-261688 A | 9/2005 |
| JP | 2013-215515 A | 10/2013 |

\* cited by examiner

BENDING OPERATION MECHANISM OF ENDOSCOPE, AND ENDOSCOPE

CROSS REFERENCE TO RELATED APPLICATION

This application is a continuation application of PCT/JP2019/006816 filed on Feb. 22, 2019 and claims benefit of Japanese Application No. 2018-093035 filed in Japan on May 14, 2018, the entire contents of which are incorporated herein by this reference.

BACKGROUND OF THE INVENTION

1. Field of the Invention

The present invention relates to a bending operation mechanism of an endoscope for bending a bending portion by pulling a wire, and an endoscope.

2. Description of the Related Art

A bending operation mechanism using a wire in an endoscope has a configuration in which the distal end portion of the wire is connected to a bending portion of the endoscope, and the proximal end portion of the wire is connected to a pulley provided to an operation portion. Pulling the wire by operating an angle operation knob for rotating the pulley causes tension in the wire, and the tension causes the bending portion to bend.

Pulling the one end side of the wire connected to the pulley may cause the other end side to loosen in such a bending operation mechanism. A technique for absorbing such slack of the wire has been conventionally proposed.

For example, the endoscope apparatus described in Japanese Unexamined Patent Application Publication No. 2005-218569 includes: a pair of operation wires each of which extends from a bending portion of an insertion portion of an endoscope and performs a bending operation of the bending portion in at least two directions; a pulley unit including a pulley on which the pair of operation wires is wound; cap portions respectively provided to each of proximal end portions of the pair of operation wires; and a locking portion held by the pulley unit in freely rotatable manner. The locking portion performs the bending operation of the bending portion by pulling or loosening each of the pair of operation wires. The pulling or loosening each of the pair of operation wires is enabled since each of the cap portions is held by the pulley unit in engaged-released changeable manner.

SUMMARY OF THE INVENTION

A bending operation mechanism of an endoscope according to one aspect of the present invention includes: a first wire including a distal end portion connected to a bending portion provided to an insertion portion of an endoscope, and configured to cause the bending portion to bend in a first direction by the first wire being pulled; a second wire including a distal end portion connected to the bending portion, and configured to cause the bending portion to bend in a second direction by the second wire being pulled; a first rotation member to which a proximal end portion of the first wire is connected, and configured to cause the first wire to be pulled by the first rotation member being rotated in the first rotation direction; a second rotation member to which a proximal end portion of the second wire is connected, and configured to cause the second wire to be pulled by the second rotation member being rotated in the second rotation direction opposite to the first rotation direction, the second rotation member having a rotation center coaxial with a rotation center of the first rotation member; and an operation member configured to rotate in the first rotation direction and the second rotation direction from a neutral position when the bending portion is not bent, the operation member including a first protrusion causing the first rotation member to rotate in the first rotation direction and a second protrusion causing the second rotation member to rotate in the second rotation direction, the second protrusion being provided at a different position from the first protrusion in a rotation axis direction of the operation member. A first hole for receiving the operation member is formed in the first rotation member and a first engagement portion for the first protrusion to engage with when the operation member rotates in the first rotation direction is formed in the first hole. A second hole for receiving the operation member is formed in the second rotation member and a second engagement portion for the second protrusion to engage with when the operation member rotates in the second rotation direction is formed in the second hole. The first protrusion and the first engagement portion engage with each other and the second protrusion and the second engagement portion do not engage with each other when the operation member rotates in the first rotation direction relative to the neutral position, and the second protrusion and the second engagement portion engage with each other and the first protrusion and the first engagement portion do not engage with each other when the operation member rotates in the second rotation direction relative to the neutral position.

An endoscope according to one aspect of the present invention includes the bending operation mechanism of the endoscope described above.

DETAILED DESCRIPTION OF THE PREFERRED EMBODIMENTS

Figure 1:
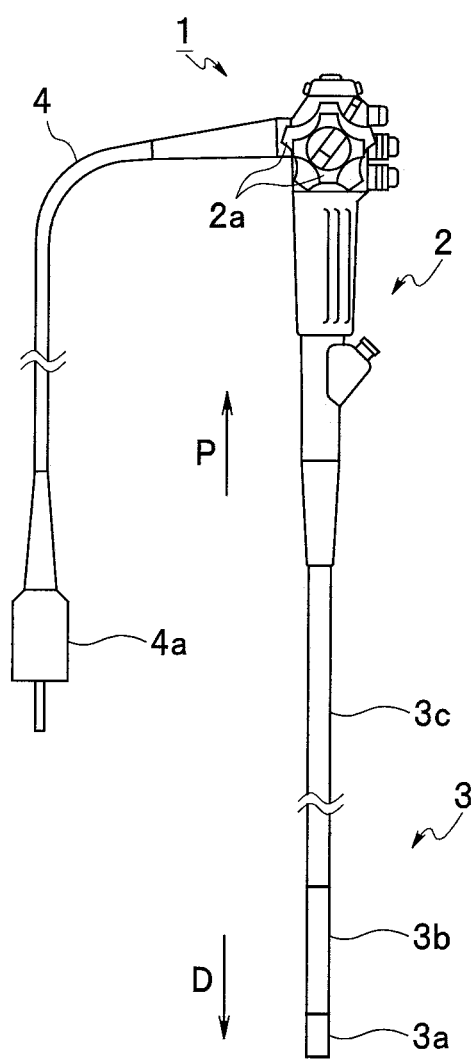
FIG. 1 is a front elevational view illustrating a configuration of an endoscope according to Embodiment 1 of the present invention.

Hereinafter, embodiments of the present invention will be described with reference to the accompanying drawings.

Note that in each of the drawings used in the following description, in order to make each constituent element sized to be recognizable in the drawings, the constituent elements may have different scales, and the present invention is not limited to only the number of constituent elements, the shape of the constituent elements, the ratio of the sizes of the constituent elements, and the relative positional relationship of each of the constituent elements described in the drawings.

Embodiment 1

FIG. 1 to FIG. 9 illustrate Embodiment 1 of the present invention, and FIG. 1 is a front elevational view illustrating a configuration of an endoscope 1.

The endoscope 1 is capable of being introduced into a subject, and is used for optically observing the inside of the subject. The subject into which the endoscope 1 is introduced is an object to be observed, and may be any of a human body, a living body other than a human body, and an artifact. Some examples of artifacts are such as machines and buildings.

In the present embodiment, the case where the endoscope 1 is an electronic endoscope that picks up an optical image of a subject will be described as an example, but the present invention is not limited thereto, and may be applied to an optical endoscope for observing an optical image.

The endoscope 1 is provided with an operation portion 2, an insertion portion 3, and a universal cord 4.

The operation portion 2 is a portion for a user to grasp and perform an operation. The operation portion 2 is provided with an angle operation knob 2a. The angle operation knob 2a is a rotation operation member for a bending operation of a bending portion 3b, which will be described later, of the insertion portion 3. The angle operation knob 2a may be any one of a lever type, a dial type, and the like.

The insertion portion 3 is provided on a distal end side of the operation portion 2, and is a portion to be introduced into a subject. The insertion portion 3 includes a distal end portion 3a, the bending portion 3b, and a flexible tube portion 3c in the order from the distal end side toward a proximal end side. Note that the distal end portion 3a side of the insertion portion 3 (side of insertion direction to a subject, far end from a user) is referred to as the distal end side, and the operation portion 2 side of the insertion portion 3 (reverse direction side of insertion direction, near end to a user) is referred to as the proximal end side. The distal end side is indicated by an arrow D, and the proximal end side is indicated by an arrow P in the drawings.

The distal end portion 3a is provided with an objective optical system and an illumination optical system, and in a case where the endoscope 1 is an electronic endoscope, an image pickup unit including such as an image pickup device for picking up an optical image formed by the objective optical system is provided.

The bending portion 3b is bent in accordance with the operation of the angle operation knob 2a of the operation portion 2 described above. In the present embodiment, it is assumed that the bending portion 3b is bendable in an up-down direction (or may be bendable in a right-left direction), for example. Note that the up-down direction or the right-left direction of the bending is set so as to coincide with the up-down direction or the right-left direction of an object image observed at a neutral position in which the bending portion 3b is not bent.

However, the bending direction is not limited to the description above, and for example, in Embodiment 2 which will be described later, an example in which the bending portion 3b is bendable in the up-down direction and the right-left direction will be described. In the configuration of Embodiment 2 which will be described later, it is possible to bend the bending portion in any direction around an insertion axis O by combining the bending in the up-down direction and the bending in the right-left direction.

The flexible tube portion 3c is a tubular portion having flexibility. A light guide for transmitting the illumination light to the objective optical system in the distal end portion 3a, a signal line for transmitting a drive signal for driving the image pickup unit in the distal end portion 3a, and a signal line for transmitting an image pickup signal obtained by the image pickup unit, for example, are inserted into the flexible tube portion 3c. Note that, although an example is cited in which the endoscope 1 is a flexible endoscope provided with the flexible tube portion 3c, the endoscope 1 may be a rigid endoscope.

The universal cord 4 extends from a side portion of the operation portion 2, for example. The universal cord 4 includes the light guide and the signal lines described above. A connector 4a for connecting to an external device is provided at the proximal end portion of the universal cord 4. The external device supplies the above-described illumination light and the drive signal, receives the above-described image pickup signal, and performs image processing and the like.

Figure 2:
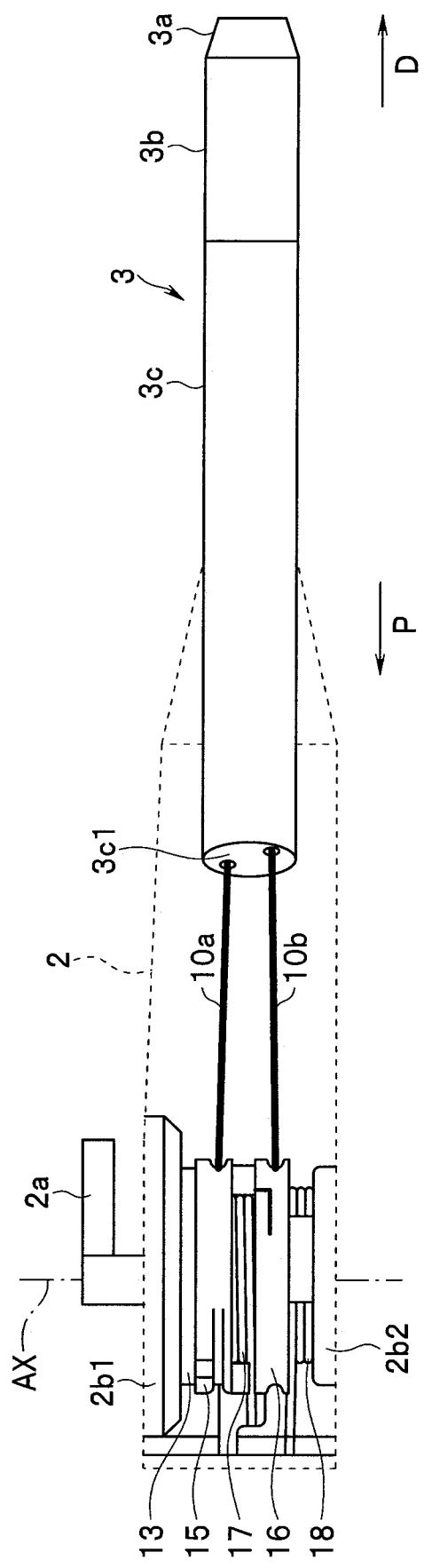
FIG. 2 is a diagram illustrating a configuration of a bending operation mechanism of the endoscope according to Embodiment 1.
Figure 3:
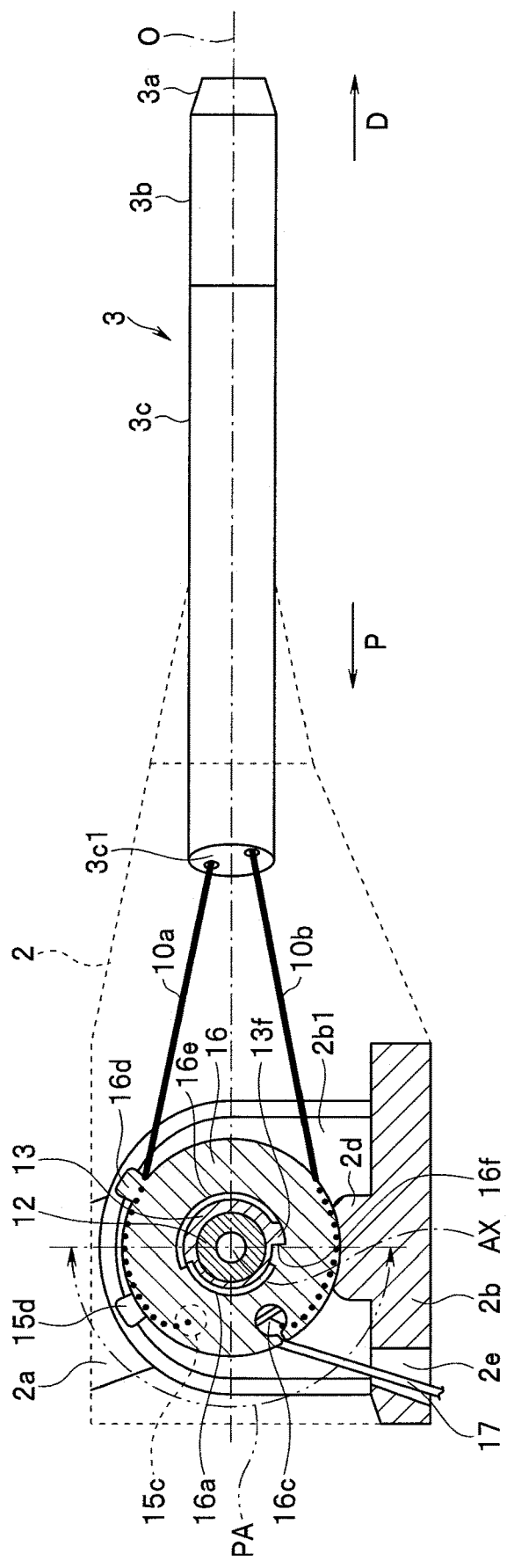
FIG. 3 is a sectional view illustrating a configuration of the bending operation mechanism of the endoscope in a neutral position according to Embodiment 1.
Figure 4:
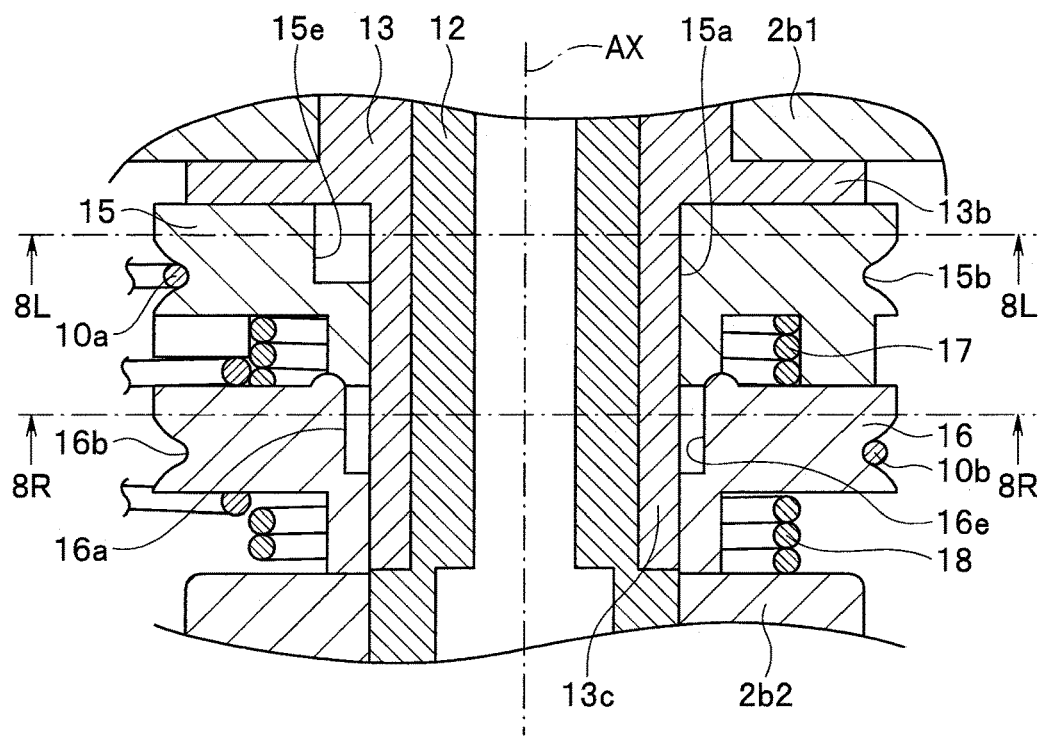
FIG. 4 is a sectional view along a rotation axis AX illustrating a configuration of the bending operation mechanism of the endoscope according to Embodiment 1.
Figure 5:
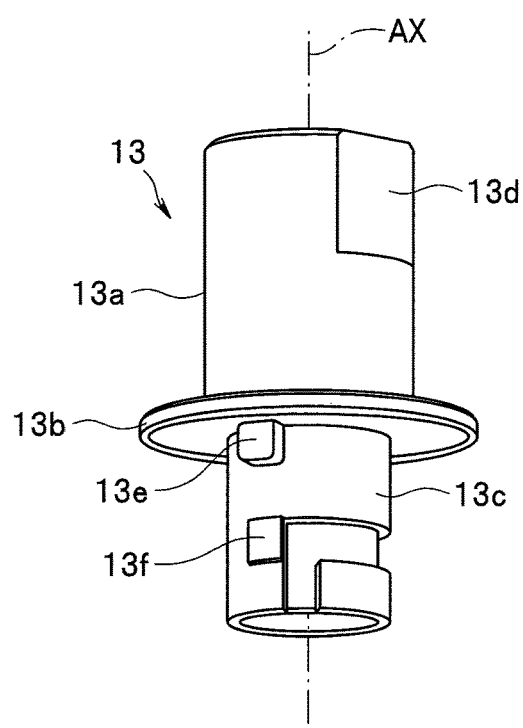
FIG. 5 is a perspective view illustrating a configuration of a rotation shaft member according to Embodiment 1.
Figure 6:
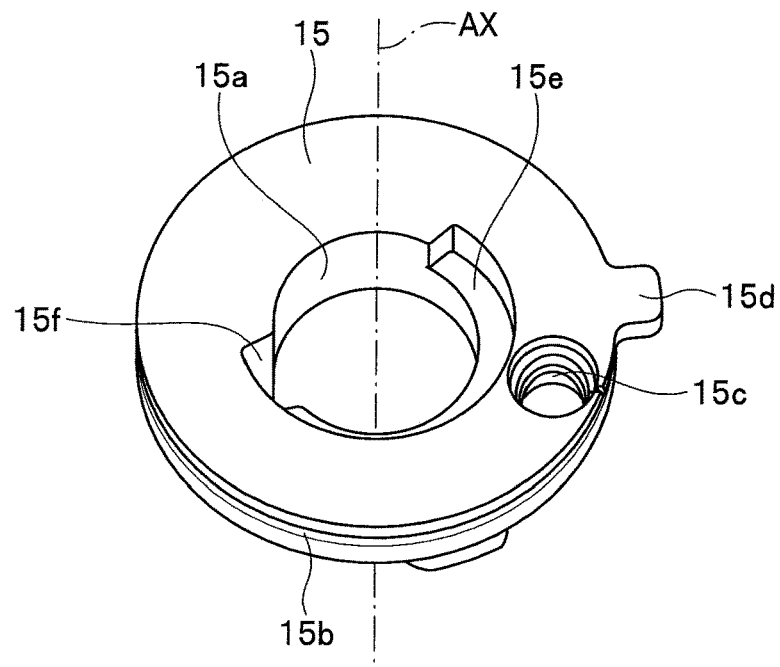
FIG. 6 is a perspective view illustrating a configuration of a first pulley according to Embodiment 1.
Figure 7:
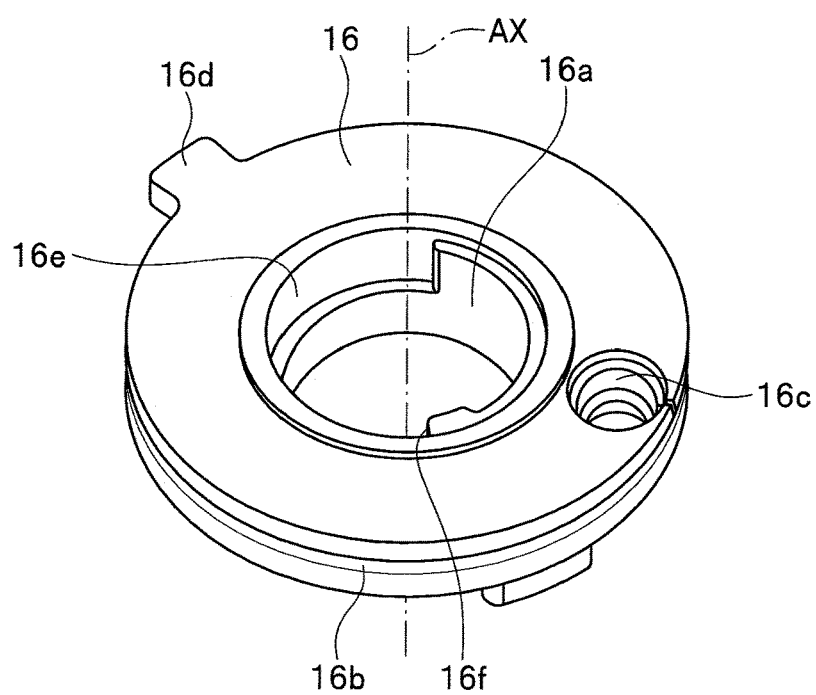
FIG. 7 is a perspective view illustrating a configuration of a second pulley according to Embodiment 1.

Next, FIG. 2 is a diagram illustrating a configuration of the bending operation mechanism of the endoscope 1, FIG. 3 is a sectional view illustrating a configuration of the bending operation mechanism of the endoscope 1 in a neutral position, FIG. 4 is a sectional view along a rotation axis AX illustrating a configuration of the bending operation mechanism of the endoscope 1, FIG. 5 is a perspective view illustrating a configuration of a rotation shaft member 13, FIG. 6 is a perspective view illustrating a configuration of a first pulley 15, and FIG. 7 is a perspective view illustrating a configuration of a second pulley 16.

The bending operation mechanism of the endoscope 1 includes a first wire 10a, a second wire 10b, the angle operation knob 2a attached to an operation portion frame 2b of the operation portion 2, a support shaft member 12, the rotation shaft member 13, the first pulley 15 serving as a first rotation member, the second pulley 16 serving as a second rotation member, a first torsion spring 17, and a second torsion spring 18.

A flange portion 13b of the rotation shaft member 13 which will be described later, the first pulley 15, the first torsion spring 17, the second pulley 16, and the second torsion spring 18 are arranged in the order from a knob side operation frame portion 2b1 toward a backside operation frame portion 2b2 of the operation portion frame 2b.

The first wire 10a passes through a manifold 3c1 provided in the insertion portion 3 of the endoscope 1, and then, the distal end portion of the first wire 10a is connected to the bending portion 3b. By pulling the first wire 10a, the bending portion 3b bends in a first direction.

The second wire 10b passes through the manifold 3c1 provided in the insertion portion 3 of the endoscope 1, and then, the distal end portion of the second wire 10b is connected to the bending portion 3b. By pulling the second wire 10b, the bending portion 3b bends in a second direction.

An example in which the first direction is an upward (U: up) direction and the second direction is a downward (D: down) direction will be described in the present embodiment. However, as described above, the first direction may be a left (L: left) direction, and the second direction may be a right (R: right) direction.

The operation portion frame 2b is provided with the support shaft member 12 that is coaxial with the rotation axis AX of the angle operation knob 2a. The support shaft member 12 is a hollow cylindrical member, for example. Further, the rotation axis AX of the angle operation knob 2a is arranged so as to be orthogonal to the insertion axis O of the insertion portion 3. Note that the support shaft member 12 may be omitted in the configuration of the present embodiment.

An inner periphery of the rotation shaft member 13 having a cylindrical shape is rotatably fit on an outer periphery of the support shaft member 12. The rotation shaft member 13 includes a knob coupling portion 13a, the flange portion 13b, and a pulley drive portion 13c as illustrated in FIG. 5.

The angle operation knob 2a is fixed to the rotation shaft member 13 by fitting to the knob coupling portion 13a. The knob coupling portion 13a is provided with a knob fitting shape portion 13d. Therefore, the angle operation knob 2a integrally rotates with the rotation shaft member 13 by fitting to the knob fitting shape portion 13d. Thus, the angle operation knob 2a is attached to the operation portion frame 2b by using the rotation shaft member 13.

The angle operation knob 2a and the rotation shaft member 13 are operation members that are rotatable in the first rotation direction and the second rotation direction from the neutral position in which the bending portion 3b is not bent.

The flange portion 13b is arranged between the first pulley 15 and the knob side operation frame portion 2b1 of the operation portion frame 2b, and prevents the first pulley 15 from sliding against the knob side operation frame portion 2b1 when the first pulley 15 rotates around the rotation axis AX.

The pulley drive portion 13c includes a first protrusion 13e for rotating the first pulley 15 in the first rotation direction, and a second protrusion 13f for rotating the second pulley 16 in the second rotation direction. The second rotation direction is opposite to the first rotation direction.

The first pulley 15 is the first rotation member to which the proximal end portion of the first wire 10a is connected. Rotating the first pulley 15 in the first rotation direction causes the first wire 10a to be pulled.

On the outer peripheral side of the first pulley 15, a wire groove 15b for winding up the first wire 10a is provided.

Further, the first pulley 15 is provided with a wire connection portion 15c for connecting the proximal end portion of the first wire 10a.

The wire connection portion 15c is arranged in a range PA on the proximal end side relative to the rotation axis AX which is the rotation center of the first pulley 15 when the angle operation knob 2a and the rotation shaft member 13 are positioned at the neutral position as illustrated in FIG. 3. Thus, the proximal end portion of the first wire 10a is connected to the first pulley 15 in the range PA on the proximal end side relative to the rotation center of the first pulley 15 when the angle operation knob 2a and the rotation shaft member 13 are positioned at the neutral position.

Further, a first hole 15a for receiving the rotation shaft member 13 is formed in the first pulley 15 as illustrated in FIG. 6.

In the first hole 15a, a first engagement portion 15f is formed. The first engagement portion 15f is engaged with the first protrusion 13e when the rotation shaft member 13 rotates in the first rotation direction.

Further, in the first hole 15a, a first inner circular portion 15e is formed on the second rotation direction side of the first engagement portion 15f. The first inner circular portion 15e has an inner radius larger than the rotation radius of the first protrusion 13e. The configuration in which the inner radius of the first inner circular portion 15e is larger than the rotation radius of the first protrusion 13e allows the first protrusion 13e to rotate separating from the first engagement portion 15f when the rotation shaft member 13 rotates in the second rotation direction.

Figure 8:
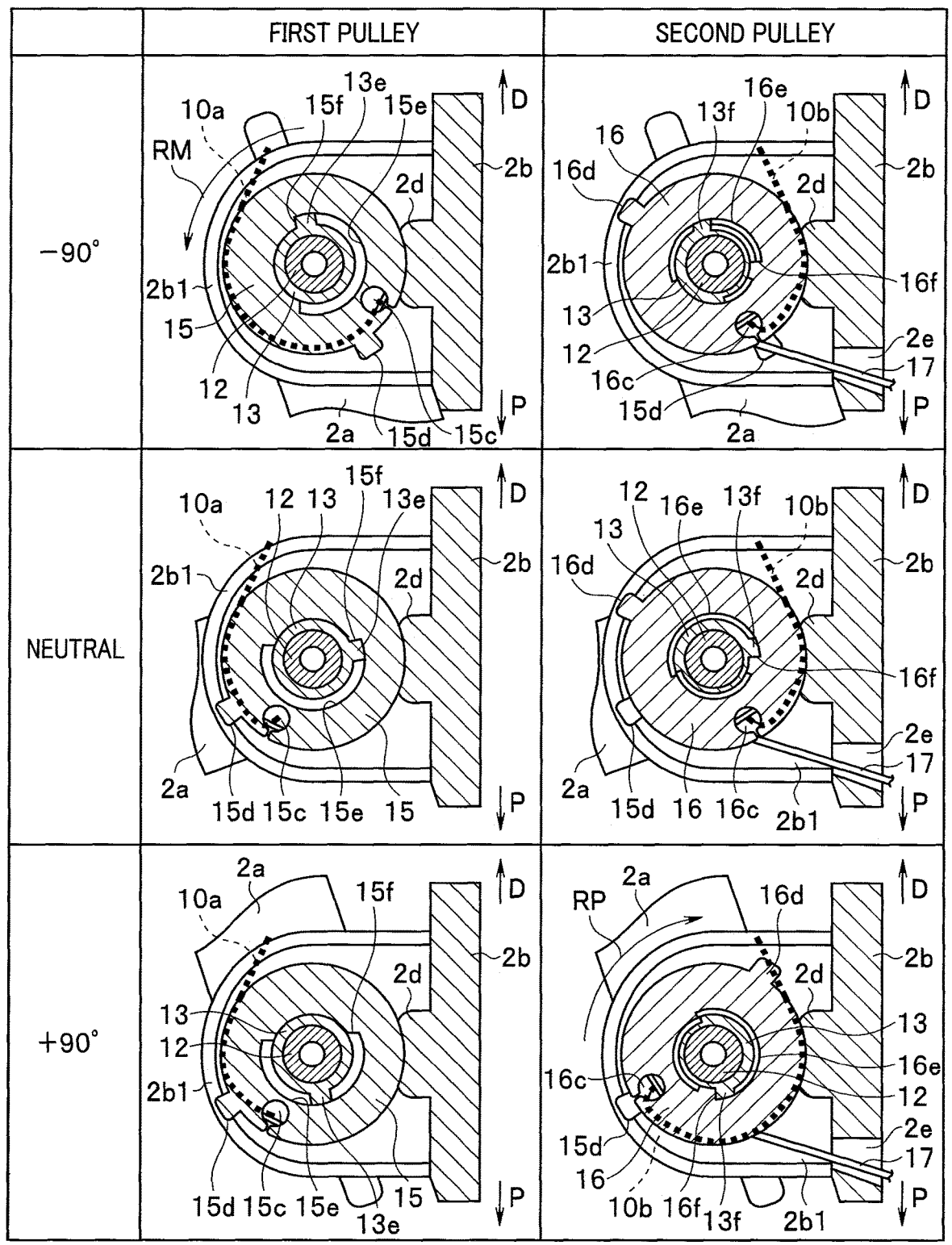
FIG. 8 is a table illustrating actions of the first pulley and the second pulley in accordance with a rotation of an angle operation knob and the rotation shaft member according to Embodiment 1.

Further, a projection 15d is provided to the outer periphery of the first pulley 15. A stopper portion 2d, as illustrated in FIG. 3 and FIG. 8 to be described later, etc., is provided to the rotation path of the projection 15d of the operation portion frame 2b. When the first pulley 15 rotates in the first rotation direction, the projection 15d abuts against the stopper portion 2d, thereby limiting the rotation range of the first pulley 15 in the first rotation direction.

The second pulley 16 is the second rotation member to which the proximal end portion of the second wire 10b is connected. Rotating the second pulley 16 in the second rotation direction causes the second wire 10b to be pulled.

Both of the rotation center of the first pulley 15 and the rotation center of the second pulley 16 coincide with the rotation axis AX. Thus, the first pulley 15 and the second pulley 16 are coaxial with each other.

On the outer peripheral side of the second pulley 16, a wire groove 16b for winding up the second wire 10b is provided. Further, the second pulley 16 is provided with a wire connection portion 16c for connecting the proximal end portion of the second wire 10b.

The wire connection portion 16c is arranged in the range PA on the proximal end side relative to the rotation axis AX which is the rotation center of the second pulley 16 when the angle operation knob 2a and the rotation shaft member 13 are positioned at the neutral position as illustrated in FIG. 3. Thus, the proximal end portion of the second wire 10b is connected to the second pulley 16 in the range PA on the proximal end side relative to the rotation center of the second pulley 16 when the angle operation knob 2a and the rotation shaft member 13 are positioned at the neutral position.

Further, a second hole 16a for receiving the rotation shaft member 13 is formed in the second pulley 16 as illustrated in FIG. 7.

In the second hole 16a, a second engagement portion 16f is formed. The second engagement portion 16f is engaged with the second protrusion 13f when the rotation shaft member 13 rotates in the second rotation direction.

Further, in the second hole 16a, a second inner circular portion 16e is formed on the first rotation direction side of the second engagement portion 16f. The second inner circular portion 16e has an inner radius larger than the rotation radius of the second protrusion 13f. The configuration in which the inner radius of the second inner circular portion 16e is larger than the rotation radius of the second protrusion 13f allows the second protrusion 13f to rotate separating from the second engagement portion 16f when the rotation shaft member 13 rotates in the first rotation direction.

A projection 16d is provided to the outer periphery of the second pulley 16. When the second pulley 16 rotates in the second rotation direction, the projection 16d abuts against the stopper portion 2d of the operation portion frame 2b described above, thereby limiting the rotation range of the second pulley 16 in the second rotation direction.

Thus, the abutting of the projection 15d of the first pulley 15 against the stopper portion 2d limits the rotation range in the first rotation direction of the rotation shaft member 13 and the angle operation knob 2a. The abutting of the projection 16d of the second pulley 16 against the stopper portion 2d limits the rotation range in the second rotation direction of the rotation shaft member 13 and the angle operation knob 2a.

The first torsion spring 17 is a first urging member to urge the first pulley 15 to return to the neutral position. Therefore, the first protrusion 13e rotates in the second rotation direction separating from the first engagement portion 15f when the angle operation knob 2a and the rotation shaft member 13 rotate in the second rotation direction relative to the neutral position.

The second torsion spring 18 is a second urging member to urge the second pulley 16 to return to the neutral position. Therefore, the second protrusion 13f rotates in the first rotation direction separating from the second engagement portion 16f when the angle operation knob 2a and the rotation shaft member 13 rotate in the first rotation direction relative to the neutral position.

Note that one end of the first torsion spring 17 and one end of the second torsion spring 18 are hooked on a spring hook 2e provided to the operation portion frame 2b as illustrated in FIG. 3, for example. Further, the provision of the first torsion spring 17 (or second torsion spring 18 in addition) eliminates the need for the thrust plate between the first pulley 15 and the second pulley 16.

Figure 9:
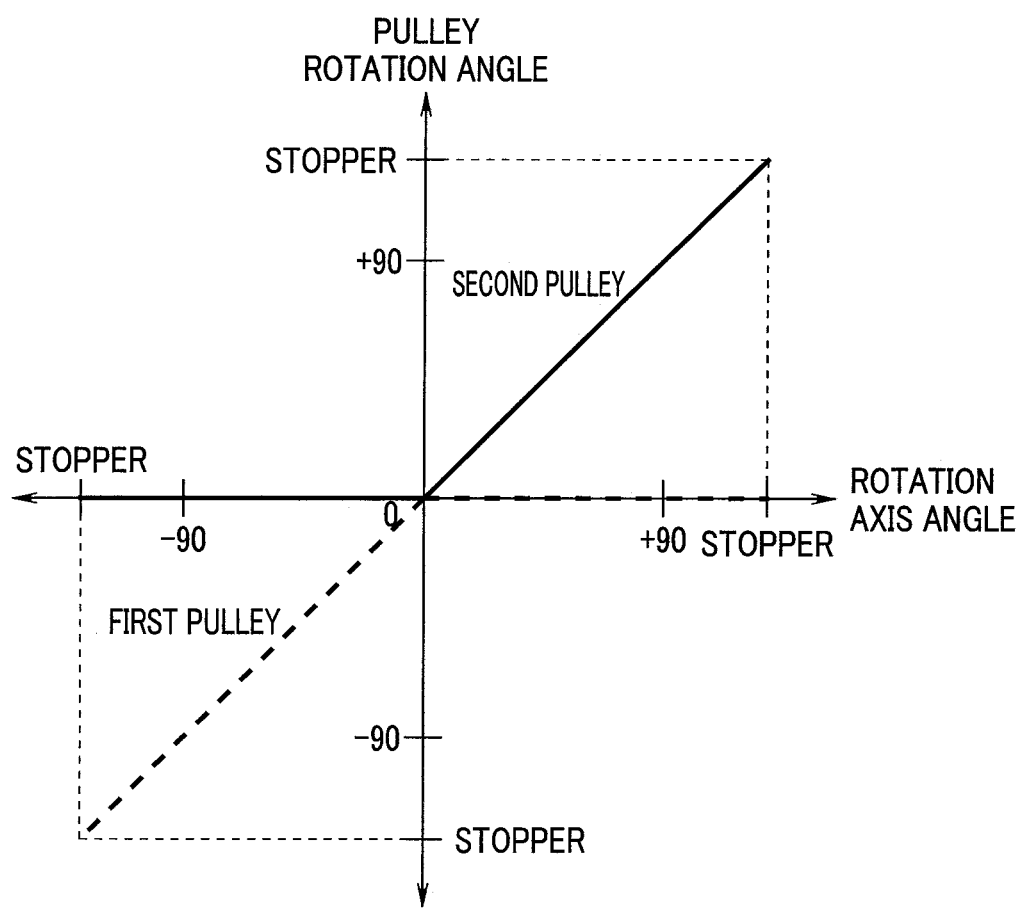
FIG. 9 is a diagram illustrating rotation angles of the first pulley and the second pulley in accordance with the rotation angle of the rotation shaft member according to Embodiment 1.

Next, FIG. 8 is a table illustrating actions of the first pulley 15 and the second pulley 16 in accordance with the rotation of the angle operation knob 2a and the rotation shaft member 13, and FIG. 9 is a diagram illustrating the rotation angles of the first pulley 15 and the second pulley 16 in accordance with the rotation angle of the rotation shaft member 13. A cross section 8L-8L in FIG. 4 is illustrated in the left column of FIG. 8 relating to the first pulley 15, and a cross section 8R-8R in FIG. 4 is illustrated in the right column of FIG. 8 relating to the second pulley 16.

Note that the rotation angles of the first pulley 15 and the second pulley 16 are illustrated with the neutral position as a reference (rotation angle of 0°) in FIG. 8 and FIG. 9. The clockwise direction is referred to as a positive direction RP of the rotation angle, and the counterclockwise direction is referred to as a negative direction RM of the rotation angle in FIG. 3 and FIG. 8.

The neutral row in FIG. 8 illustrates a status when the first pulley 15 and the second pulley 16 are positioned at the neutral position, that is, at the rotation angle of 0°. Note that the first pulley 15 and the second pulley 16 automatically return to the neutral position by the tensions of the first wire 10a and the second wire 10b when the angle operation knob 2a and the rotation shaft member 13 are returned to the neutral position.

However, even when the action of tension alone may cause the first pulley 15 and the second pulley 16 to shift from the neutral position, since the first torsion spring 17 and the second torsion spring 18 are provided as described above, the urging force of each of the springs 17 and 18 causes the first pulley 15 and the second pulley 16 to accurately return to the neutral position.

When the angle operation knob 2a and the rotation shaft member 13 rotate in the negative direction RM from the neutral position, the first protrusion 13e engages with the first engagement portion 15f, and the first pulley 15 integrally rotates with the rotation shaft member 13 (and angle operation knob 2a). At the time, the second protrusion 13f freely rotates in the second inner circular portion 16e, and the second pulley 16 does not rotate by the action of the rotation shaft member 13 (see −90° row in FIG. 8, and FIG. 9) since the second protrusion 13f and the second pulley 16 do not engage with each other. However, when the second wire 10b moves in accordance with the bending of the bending portion 3b, the second pulley 16 may rotate following the tension of the second wire 10b. Thus, the negative direction RM illustrated in FIG. 8 and FIG. 9 corresponds to the first rotation direction described above.

On the other hand, when the angle operation knob 2a and the rotation shaft member 13 rotate in the positive direction RP from the neutral position, the second protrusion 13f engages with the second engagement portion 16f, and the second pulley 16 integrally rotates with the rotation shaft member 13 (and angle operation knob 2a). At the time, the first protrusion 13e freely rotates in the first inner circular portion 15e, and the first pulley 15 does not rotate by the action of the rotation shaft member 13 (see +90° row in FIG. 8, and FIG. 9) since the first protrusion 13e and the first pulley 15 do not engage with each other. However, when the first wire 10a moves in accordance with the bending of the bending portion 3b, the first pulley 15 may rotate following the tension of the first wire 10a. Thus, the positive direction RP illustrated in FIG. 8 and FIG. 9 corresponds to the second rotation direction described above.

According to such Embodiment 1, when the rotation shaft member 13 rotates in the first rotation direction, the first pulley 15 rotates with the first protrusion 13e engaged with the first engagement portion 15f and the second pulley 16 basically does not rotate with the second protrusion 13f freely rotating in the second inner circular portion 16e. Further, when the rotation shaft member 13 rotates in the second rotation direction, the second pulley 16 rotates with the second protrusion 13f engaged with the second engagement portion 16f and the first pulley 15 basically does not rotate with the first protrusion 13e freely rotating in the first inner circular portion 15e. Thus, the application of compression force to the first and second wires 10a and 10b is prevented, to thereby be capable of preventing the derailment of the first and the second wires 10a and 10b from the first and second pulleys 15 and 16. As a result, the bending operation mechanism of the endoscope 1 can maintain the high accuracy in the bending operation even when the bending operation is repeated.

In addition, the operation of the one angle operation knob 2a alone may control both of the first wire 10a and the second wire 10b since the first protrusion 13e for rotating the first pulley 15 in the first rotation direction and the second protrusion 13f for rotating the second pulley 16 in the second rotation direction are provided to the rotation shaft member 13. The user interface of the bending operation mechanism of the present embodiment, therefore, may be made substantially equivalent to that of the existing bending operation mechanism.

Further, the first protrusion 13e rotates in the second rotation direction separating from the first engagement portion 15f when the rotation shaft member 13 rotates in the second rotation direction relative to the neutral position, and the second protrusion 13f rotates in the first rotation direction separating from the second engagement portion 16f when the rotation shaft member 13 rotates in the first rotation direction relative to the neutral position. The configuration makes it possible to accurately prevent the compression force from being applied to the first and second wires 10a and 10b with the neutral position being a boundary.

Meanwhile, positioning of the connection portion between the wire and the pulley on the distal end side relative to the rotation axis AX when the rotation shaft member 13 is in the neutral position may cause the wire to easily loosen. According to the present embodiment, to the contrary, the wire connection portions 15c and 16c are arranged so as to be positioned in the range PA on the proximal end side relative to the rotation axis AX when the rotation shaft member 13 is in the neutral position. As a result, it is possible to prevent the first and second wires 10a and 10b from loosening.

Further, the first pulley 15 and the second pulley 16 may accurately be returned to the neutral position when the angle operation knob 2a and the rotation shaft member 13 are positioned at the neutral position since the first torsion spring 17 and the second torsion spring 18 are provided.

In addition, a bending operation mechanism of the endoscope 1 with low failure rate is achieved in which the up-down (UD) operation with high accuracy may be performed when the first direction is denoted as the upward direction and the second direction is denoted as the downward direction.

Meanwhile, a bending operation mechanism of the endoscope 1 with low failure rate is achieved in which the right-left (RL) operation with high accuracy may be performed when the first direction is denoted as the left direction and the second direction is denoted as the right direction.

Embodiment 2

Figure 10:
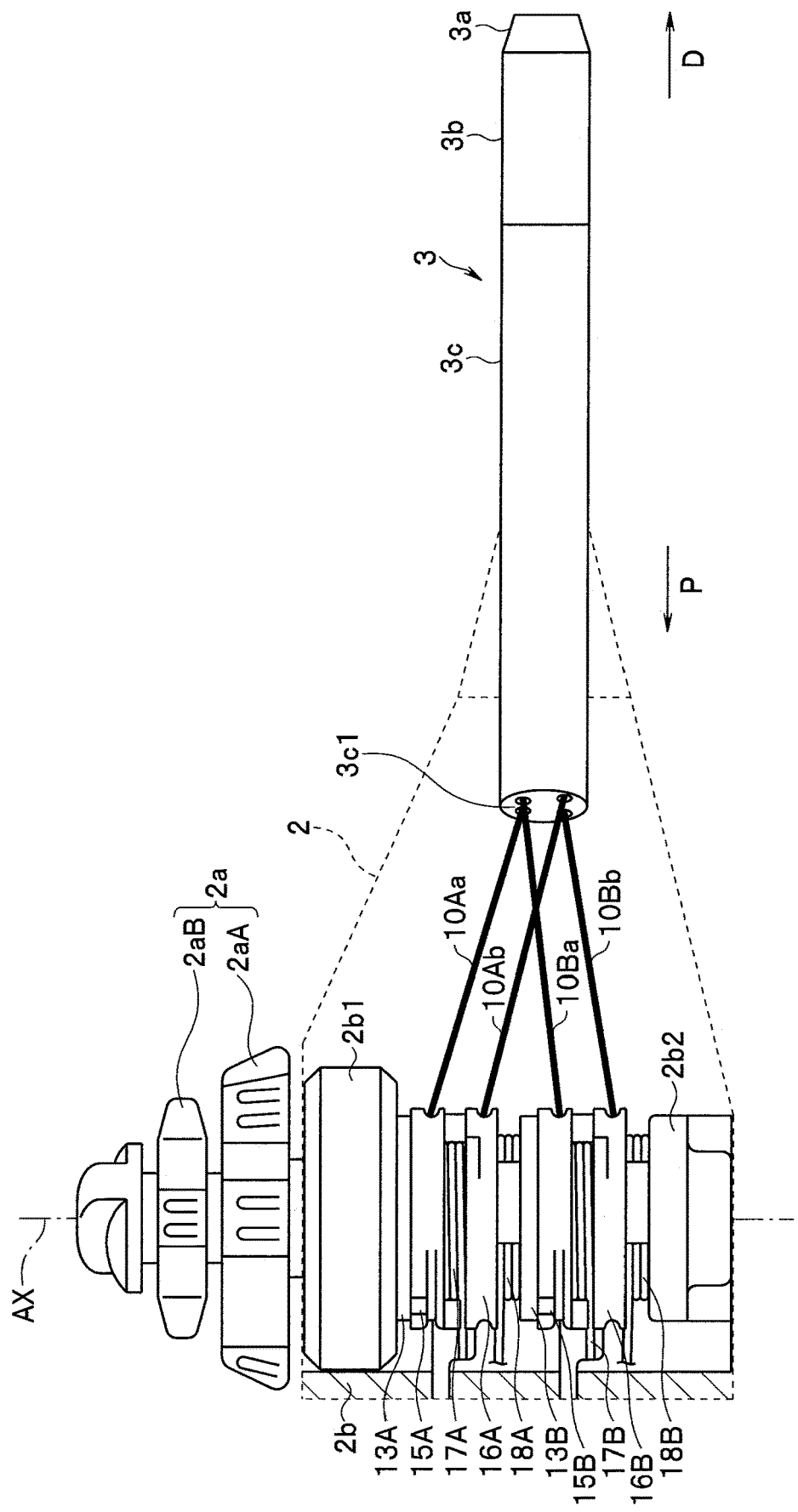
FIG. 10 is a diagram illustrating a configuration of a bending operation mechanism of an endoscope according to Embodiment 2 of the present invention.

FIG. 10 to FIG. 14 illustrate Embodiment 2 of the present invention, and FIG. 10 is a diagram illustrating a configuration of a bending operation mechanism of the endoscope 1.

In the Embodiment 2, the same components as those in the Embodiment 1 described above are denoted by the same reference numerals, and description thereof will appropriately be omitted, and only differences will be mainly described.

In the Embodiment 1 described above, the bending direction of the bending portion 3b is the up-down direction (or right-left direction), i.e., two directions, but in the present embodiment, the bending direction of the bending portion 3b is the up-down direction and the right-left direction, i.e., four directions. The present embodiment consequently has a configuration in which the combination of the bending in the up-down direction and the bending in the right-left direction enables the bending in any direction around the insertion axis O.

To achieve the configuration, the bending operation mechanism of the endoscope 1 of the present embodiment includes a first bending operation mechanism portion for bending in the up-down direction and a second bending operation mechanism portion for bending in the right-left direction.

The first bending operation mechanism portion includes a first group first wire 10Aa, a first group second wire 10Ab, a UD angle operation knob 2aA, a first rotation shaft member 13A, a first group first pulley 15A serving as a first rotation member, a first group second pulley 16A serving as a second rotation member, a first group first torsion spring 17A, and a first group second torsion spring 18A.

The second bending operation mechanism portion includes a second group first wire 10Ba, a second group second wire 10Bb, an RL angle operation knob 2aB, a second rotation shaft member 13B, a second group first pulley 15B serving as a first rotation member, a second group second pulley 16B serving as a second rotation member, a second group first torsion spring 17B, and a second group second torsion spring 18B.

The angle operation knob 2a according to the present embodiment includes the UD angle operation knob 2aA for operating the bending in the up-down direction and the RL angle operation knob 2aB for operating the bending in the right-left direction.

Figure 11:
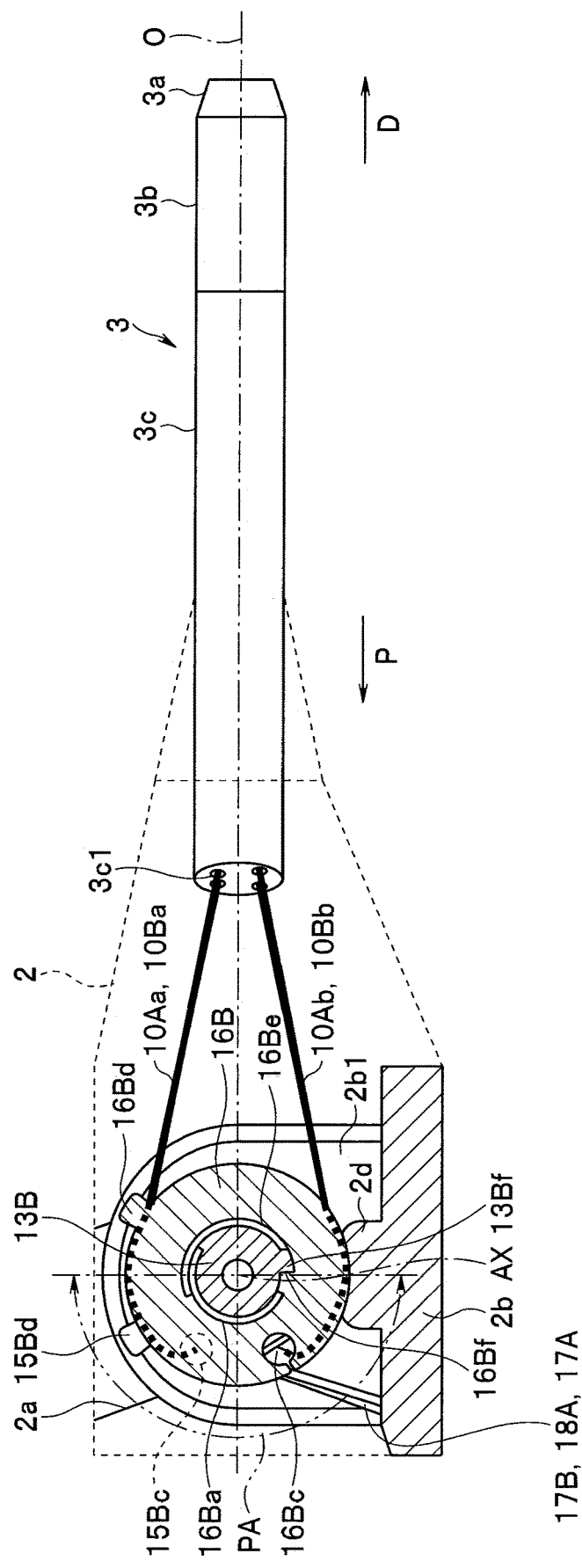
FIG. 11 is a sectional view illustrating a configuration of the bending operation mechanism of the endoscope in a neutral position according to Embodiment 2.
Figure 12:
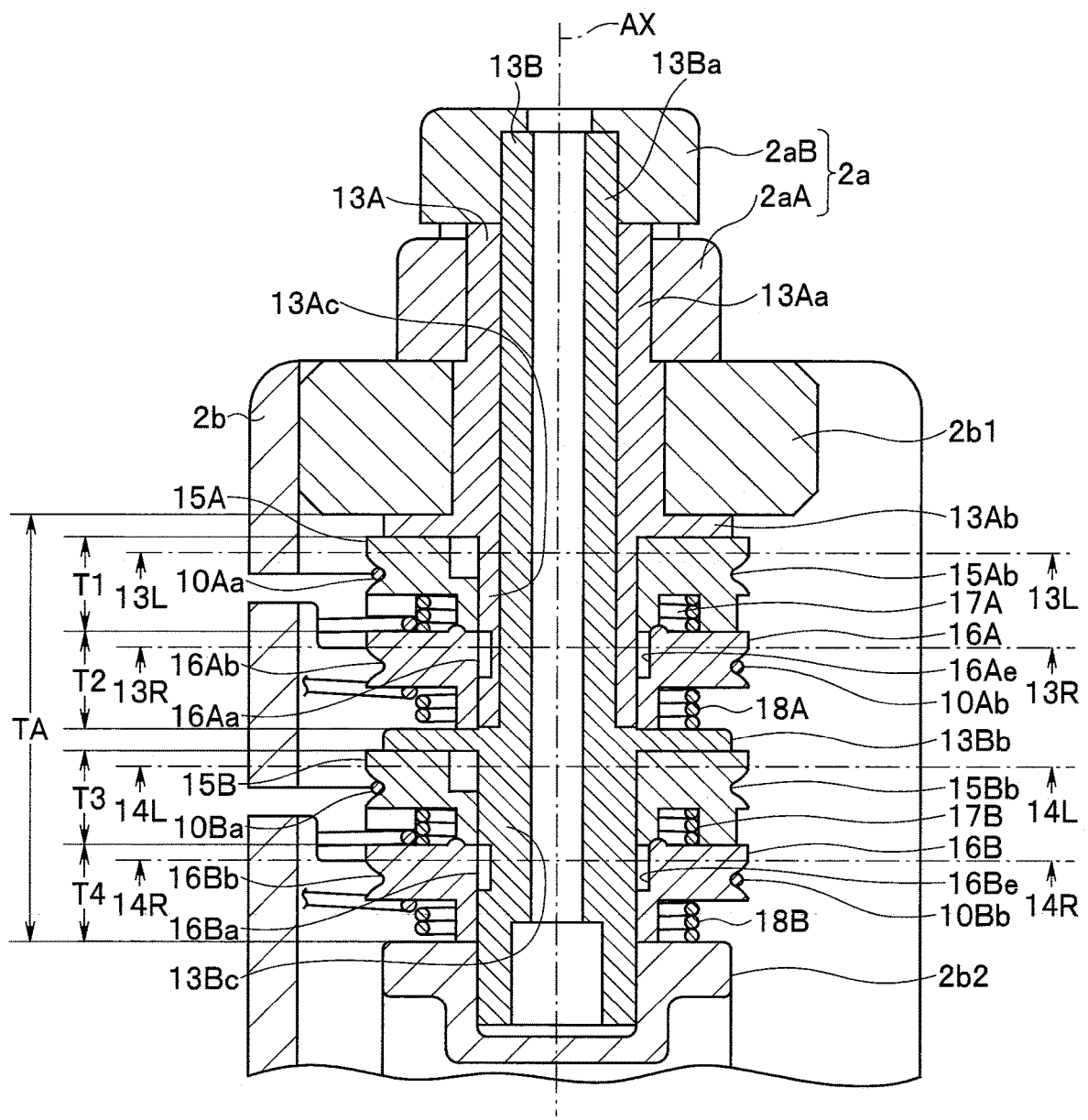
FIG. 12 is a sectional view along a rotation axis AX illustrating a configuration of the bending operation mechanism of the endoscope according to Embodiment 2.

FIG. 11 is a sectional view illustrating a configuration of the bending operation mechanism of the endoscope 1 in the neutral position, and FIG. 12 is a sectional view along the rotation axis AX illustrating the configuration of the bending operation mechanism of the endoscope 1.

The UD angle operation knob 2aA is fixed to the first rotation shaft member 13A in a knob coupling portion 13Aa to be able to integrally rotate, and the RL angle operation knob 2aB is fixed to the second rotation shaft member 13B in a knob coupling portion 13Ba to be able to integrally rotate. Note that a knob fitting shape portion similar to the knob fitting shape portion 13d in the knob coupling portion 13a of Embodiment 1 described above, not illustrated in the drawings, is provided to the knob coupling portion 13Aa and the knob coupling portion 13Ba, respectively.

An outer peripheral plane of the knob coupling portion 13Ba of the second rotation shaft member 13B having a cylindrical shape is slidably fit to an inner peripheral plane of the first rotation shaft member 13A having a cylindrical shape.

The first group first pulley 15A, the first group first torsion spring 17A, the first group second pulley 16A, and the first group second torsion spring 18A are arranged in the order along the rotation axis AX, on the outer peripheral side of a pulley drive portion 13Ac of the first rotation shaft member 13A, between a flange portion 13Ab of the first rotation shaft member 13A and a flange portion 13Bb of the second rotation shaft member 13B.

The second group first pulley 15B, the second group first torsion spring 17B, the second group second pulley 16B, and the second group second torsion spring 18B are arranged in the order along the rotation axis AX, on the outer peripheral side of a pulley drive portion 13Bc of the second rotation shaft member 13B, between the flange portion 13Bb of the second rotation shaft member 13B and the backside operation frame portion 2b2.

Note that in the present embodiment, four pulleys, that is, the first group first pulley 15A, the first group second pulley 16A, the second group first pulley 15B, and the second group second pulley 16B are arranged along the rotation axis AX, and the number of pulleys is larger than that of the existing configuration in which the up-down (UD) operation and the right-left (RL) operation are performed by two pulleys. Therefore, the thickness T1 of the first group first pulley 15A, the thickness T2 of the first group second pulley 16A, the thickness T3 of the second group first pulley 15B, and the thickness T4 of the second group second pulley 16B in the direction along the rotation axis AX are preferably set to equal to or less than 7 mm, respectively, for example, and the distance TA between the knob side operation frame portion 2b1 and the backside operation frame portion 2b2 is preferably about 28 mm By adopting the configuration described above, it is possible to keep the size of the operation portion 2 in the direction of the rotation axis AX substantially equivalent to that of the conventional operation portion, and to ensure the practical operability substantially equivalent to that in the conventional operation portion.

At least one (preferably both) of making the first group first pulley 15A and the second group first pulley 15B as a common component, and making the first group second pulley 16A and the second group second pulley 16B as a common component is preferably be performed. Thus, mass productivity is improved and a component cost may be reduced. For the purpose, the outer periphery of the pulley drive portion 13Ac and the outer periphery of the pulley drive portion 13Bc are made identical in diameter. In addition, a first protrusion 13Ae (see also FIG. 13 and FIG. 14 in the following description) and a second protrusion 13Af provided to the outer periphery of the pulley drive portion 13Ac, and a first protrusion 13Be and a second protrusion 13Bf provided to the outer periphery of the pulley drive portion 13Bc need to be appropriately arranged.

A first hole 15Aa for receiving the first rotation shaft member 13A is formed on the inner peripheral side of the first group first pulley 15A. A second hole 16Aa for receiving the first rotation shaft member 13A is formed on the inner peripheral side of the first group second pulley 16A. A wire groove 15Ab for winding up the first group first wire 10Aa is provided on the outer peripheral side of the first group first pulley 15A, and a wire groove 16Ab for winding up the first group second wire 10Ab is provided on the outer peripheral side of the first group second pulley 16A, respectively.

A first hole 15Ba for receiving the second rotation shaft member 13B is formed on the inner peripheral side of the second group first pulley 15B. A second hole 16Ba for receiving the second rotation shaft member 13B is formed on the inner peripheral side of the second group second pulley 16B. A wire groove 15Bb for winding up the second group first wire 10Ba is provided on the outer peripheral side of the second group first pulley 15B, and a wire groove 16Bb for winding up the second group second wire 10Bb is provided on the outer peripheral side of the second group second pulley 16B, respectively.

The proximal end portion of the first group first wire 10Aa is connected to a wire connection portion 15Ac of the first group first pulley 15A, and the proximal end portion of the first group second wire 10Ab is connected to a wire connection portion 16Ac of the first group second pulley 16A.

The proximal end portion of the second group first wire 10Ba is connected to a wire connection portion 15Bc of the second group first pulley 15B, and the proximal end portion of the second group second wire 10Bb is connected to a wire connection portion 16Bc of the second group second pulley 16B.

The wire connection portion 15Ac, the wire connection portion 16Ac, the wire connection portion 15Bc, and the wire connection portion 16Bc are arranged in the range PA on the proximal end side relative to the rotation axis AX when the angle operation knob 2a and the rotation shaft member 13 are positioned at the neutral position, similarly to Embodiment 1 described above.

Further, a projection 15Ad for abutting against the stopper portion 2d, a first inner circular portion 15Ae having an inner radius larger than the rotation radius of the first protrusion 13Ae, and a first engagement portion 15Af for the first protrusion 13Ae to engage with are provided to the first group first pulley 15A, similarly to the first pulley 15 in Embodiment 1 described above.

A projection 16Ad for abutting against the stopper portion 2d, a second inner circular portion 16Ae having an inner radius larger than the rotation radius of the second protrusion 13Af, and a second engagement portion 16Af for the second protrusion 13Af to engage with are provided to the first group second pulley 16A, similarly to the second pulley 16 in Embodiment 1 described above.

A projection 15Bd for abutting against the stopper portion 2d, a first inner circular portion 15Be having an inner radius larger than the rotation radius of the first protrusion 13Be, and a first engagement portion 15Bf for the first protrusion 13Be to engage with are provided to the second group first pulley 15B, similarly to the first pulley 15 in Embodiment 1 described above.

A projection 16Bd for abutting against the stopper portion 2d, a second inner circular portion 16Be having an inner radius larger than the rotation radius of the second protrusion 13Bf, and a second engagement portion 16Bf for the second protrusion 13Bf to engage with are provided to the second group second pulley 16B, similarly to the second pulley 16 in Embodiment 1 described above.

Figure 13:
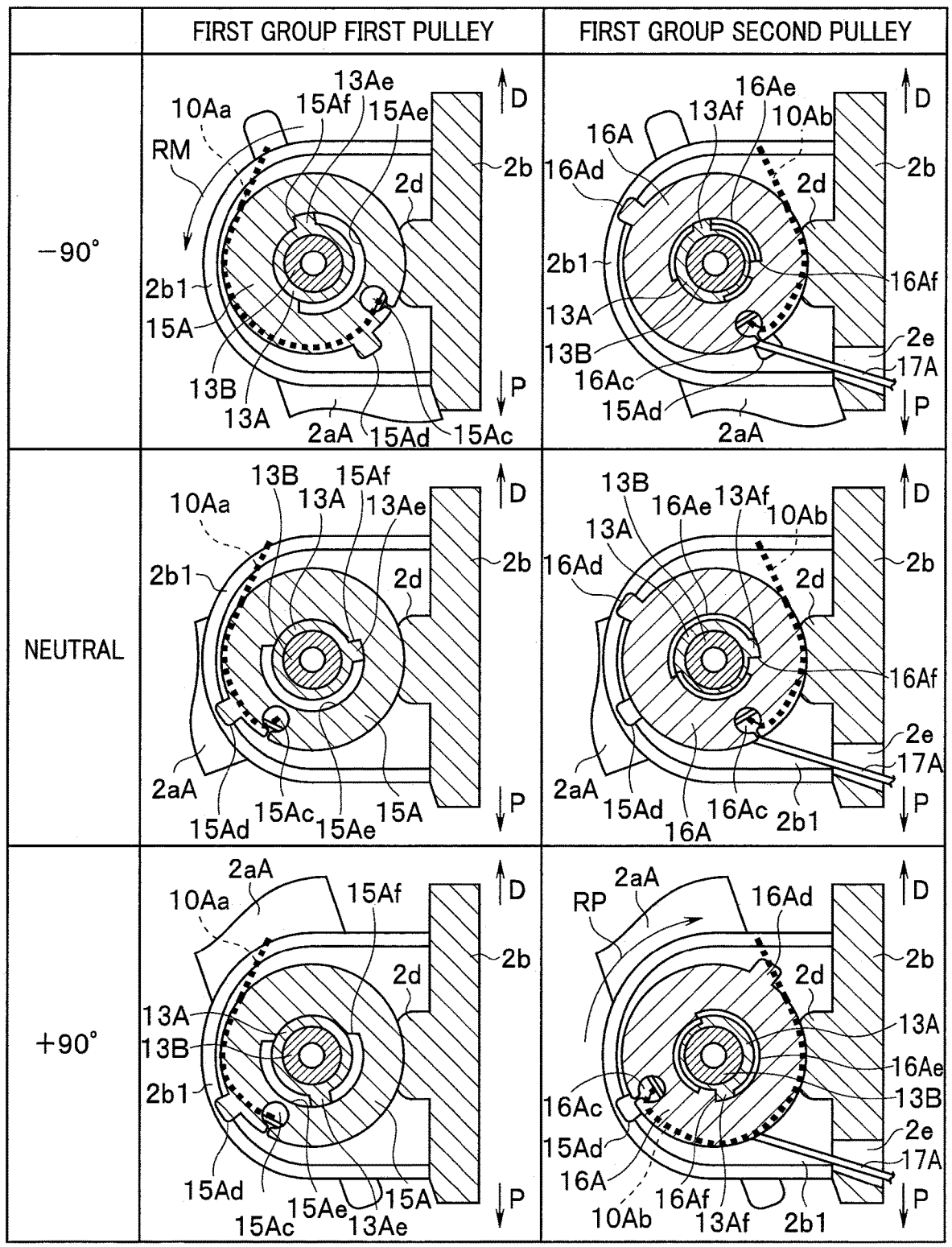
FIG. 13 is a table illustrating actions of a first group first pulley and a first group second pulley in accordance with a rotation of a UD angle operation knob and a first rotation shaft member according to Embodiment 2.

Next, FIG. 13 is a table illustrating actions of the first group first pulley 15A and the first group second pulley 16A in accordance with the rotation of the UD angle operation knob 2aA and the first rotation shaft member 13A. A cross section 13L-13L in FIG. 12 is illustrated in the left column of FIG. 13 relating to the first group first pulley 15A, and a cross section 13R-13R in FIG. 12 is illustrated in the right column of FIG. 13 relating to the first group second pulley 16A.

The neutral row in FIG. 13 illustrates a status when the first group first pulley 15A and the first group second pulley 16A are positioned at the neutral position, that is, at the rotation angle of 0°.

Note that the first group first pulley 15A and the first group second pulley 16A accurately return to the neutral position in the same manner as in Embodiment 1 described above since the first group first torsion spring 17A and the first group second torsion spring 18A are provided. Further, the provision of the first group first torsion spring 17A (or first group second torsion spring 18A in addition) eliminates the need for the thrust plate between the first group first pulley 15A and the first group second pulley 16A.

When the UD angle operation knob 2aA and the first rotation shaft member 13A rotate in the negative direction RM from the neutral position, the first protrusion 13Ae engages with the first engagement portion 15Af, and the first group first pulley 15A integrally rotates with the first rotation shaft member 13A (and UD angle operation knob 2aA). At the time, the second protrusion 13Af freely rotates in the second inner circular portion 16Ae and the first group second pulley 16A does not rotate by the action of the first rotation shaft member 13A (see −90° row in FIG. 13) since the second protrusion 13Af and the first group second pulley 16A do not engage with each other. However, when the first group second wire 10Ab moves in accordance with the bending of the bending portion 3b, the first group second pulley 16A may rotate following the tension of the first group second wire 10Ab. Thus, the negative direction RM illustrated in FIG. 13 corresponds to the first rotation direction.

On the other hand, when the UD angle operation knob 2aA and the first rotation shaft member 13A rotate in the positive direction RP from the neutral position, the second protrusion 13Af engages with the second engagement portion 16Af, and the first group second pulley 16A integrally rotates with the first rotation shaft member 13A (and UD angle operation knob 2aA). At the time, the first protrusion 13Ae freely rotates in the first inner circular portion 15Ae and the first group first pulley 15A does not rotate by the action of the first rotation shaft member 13A (see +90° row in FIG. 13) since the first protrusion 13Ae and the first group first pulley 15A do not engage with each other. However, when the first group first wire 10Aa moves in accordance with the bending of the bending portion 3b, the first group first pulley 15A may rotate following the tension of the first group first wire 10Aa. Thus, the positive direction RP illustrated in FIG. 13 corresponds to the second rotation direction.

Figure 14:
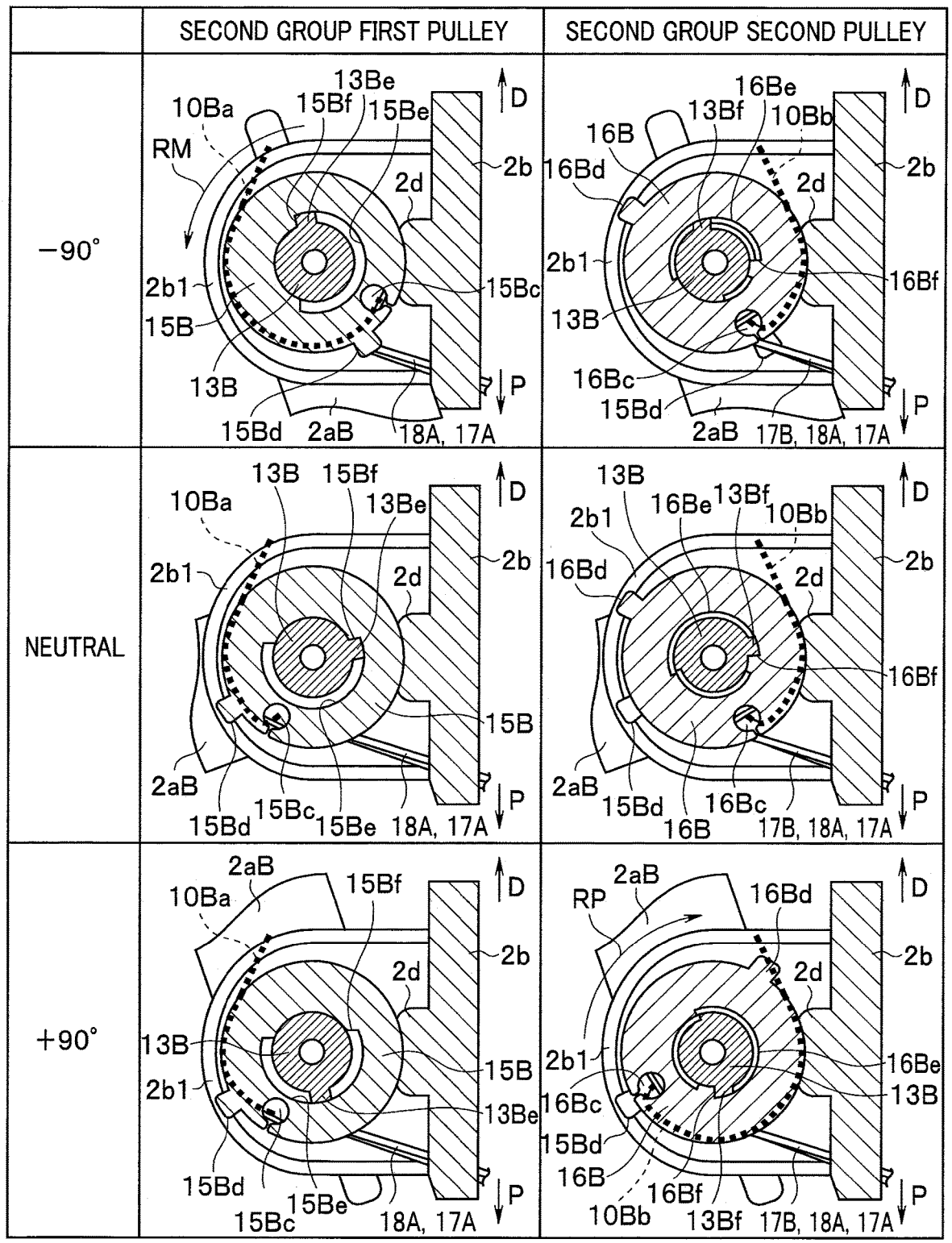
FIG. 14 is a table illustrating actions of a second group first pulley and a second group second pulley in accordance with a rotation of an RL angle operation knob and a second rotation shaft member according to Embodiment 2.

Next, FIG. 14 is a table illustrating actions of the second group first pulley 15B and the second group second pulley 16B in accordance with the rotation of the RL angle operation knob 2aB and the second rotation shaft member 13B. A cross section 14L-14L in FIG. 12 is illustrated in the left column of FIG. 14 relating to the second group first pulley 15B, and a cross section 14R-14R in FIG. 12 is illustrated in the right column of FIG. 14 relating to the second group second pulley 16B.

The neutral row in FIG. 14 illustrates a status when the second group first pulley 15B and the second group second pulley 16B are positioned at the neutral position, that is, at the rotation angle of 0°.

Note that the second group first pulley 15B and the second group second pulley 16B accurately return to the neutral position in the same manner as in Embodiment 1 described above since the second group first torsion spring 17B and the second group second torsion spring 18B are provided. Further, the provision of the second group first torsion spring 17B (or second group second torsion spring 18B in addition) eliminates the need for the thrust plate between the second group first pulley 15B and the second group second pulley 16B.

When the RL angle operation knob 2aB and the second rotation shaft member 13B rotate in the negative direction RM from the neutral position, the first protrusion 13Be engages with the first engagement portion 15Bf, and the second group first pulley 15B integrally rotates with the second rotation shaft member 13B (and RL angle operation knob 2aB). At the time, the second protrusion 13Bf freely rotates in the second inner circular portion 16Be and the second group second pulley 16B does not rotate by the action of the second rotation shaft member 13B (see −90° row in FIG. 14) since the second protrusion 13Bf and the second group second pulley 16B do not engage with each other. However, when the second group second wire 10Bb moves in accordance with the bending of the bending portion 3b, the second group second pulley 16B may rotate following the tension of the second group second wire 10Bb. Thus, the negative direction RM illustrated in FIG. 14 corresponds to the first rotation direction.

On the other hand, when the RL angle operation knob 2aB and the second rotation shaft member 13B rotate in the positive direction RP from the neutral position, the second protrusion 13Bf engages with the second engagement portion 16Bf, and the second group second pulley 16B integrally rotates with the second rotation shaft member 13B (and RL angle operation knob 2aB). At the time, the first protrusion 13Be freely rotates in the first inner circular portion 15Be and the second group first pulley 15B does not rotate by the action of the second rotation shaft member 13B (see +90° row in FIG. 14) since the first protrusion 13Be and the second group first pulley 15B do not engage with each other. However, when the second group first wire 10Ba moves in accordance with the bending of the bending portion 3b, the second group first pulley 15B may rotate following the tension of the second group first wire 10Ba. Thus, the positive direction RP illustrated in FIG. 14 corresponds to the second rotation direction.

According to such Embodiment 2, substantially the same effect as that of Embodiment 1 described above may be exhibited, and a bending operation mechanism of the endoscope 1 with low failure rate is achieved in which a combination of the up-down (UD) operation and the right-left (RL) operation with high accuracy may be performed.

Each of the thicknesses of the pulleys 15A, 16A, 15B, and 16B is made equal to or less than 7 mm, and the knob side operation frame portion 2b1 and the backside operation frame portion 2b2 are configured such that the distance TA therebetween is about 28 mm. The configuration makes it possible to keep the size of the operation portion 2 in the direction of the rotation axis AX substantially equivalent to that of the conventional operation portion, and to ensure the practical operability substantially equivalent to that in the conventional operation portion.

In the description above, each of the wire connection portions is arranged so as to be in the range PA on the proximal end side relative to the rotation axis AX in the neutral position, and the arrangement is a preferred arrangement example. However, arranging each of the wire connection portions in the neutral position outside the range PA is not prohibited, and may be accepted for a design reason or other reason.

Further, although the bending operation mechanism of the endoscope 1 has been described above, the application field of the bending operation mechanism is not limited to the endoscope 1. The bending operation mechanism is also applicable to the field of a wire pulling operation mechanism that requires high accuracy and reliability, such as an electric manipulator and a robot arm, for example.

Further, in the above, an example is described as follows. The rotation shaft member as the operation member is provided with the first protrusion and the second protrusion. The first engagement portion for the first protrusion to engage with and the first inner circular portion having an inner radius larger than the rotation radius of the first protrusion are formed in the first pulley as the first rotation member. The second engagement portion for the second protrusion to engage with and the second inner circular portion having an inner radius larger than the rotation radius of the second protrusion are formed in the second pulley as the second rotation member. However, the present invention is not limited to the example. For example, the following configuration functioning as the same as the above is acceptable. The first protrusion is provided on the inner circular side of the first pulley being the first rotation member, and the second protrusion is provided on the inner circular side of the second pulley being the second rotation member, respectively. The first engagement portion for engaging with the first protrusion and the first outer circular portion having the outer radius smaller than the rotation radius of the first protrusion and the second engagement portion for engaging with the second protrusion and the second outer circular portion having the outer radius smaller than the rotation radius of the second protrusion are formed in the rotation shaft member. Alternatively, with another configuration, the operation member may engage only with the first rotation member upon rotating in the first rotation direction, and the operation member may engage only with the second rotation member upon rotating in the second rotation direction.

The present invention is not limited to the embodiments described above as they are, and the constituent elements can be modified and embodied without departing from the spirit and scope of the present invention in the implementation stage. Various aspects of the invention can be formed by appropriate combinations of the plurality of constituent elements disclosed in the embodiments described above. For example, some constituent elements may be deleted from all the constituent elements described in the embodiment. Further, the constituent elements in different embodiments may be combined as appropriate. It goes without saying that various modifications and applications can be made without departing from the spirit of the invention.

What is claimed is:

1. A bending operation mechanism for use with an endoscope, the bending operation mechanism comprising:
    a first cylindrical disk connected to a first proximal end portion of a first wire, the first cylindrical disk configured to move the first wire in response to a first rotation of the first cylindrical disk in a first rotation direction, the first cylindrical disk having a first inner peripheral surface forming a first hole, the first inner peripheral surface including a first engagement surface;
    a second cylindrical disk connected to a second proximal end portion of a second wire, the second cylindrical disk configured to move the second wire in response to a second rotation of the second cylindrical disk in a second rotation direction opposite to the first rotation direction, the second cylindrical disk having a second inner peripheral surface forming a second hole, the second inner peripheral surface including a second engagement surface, and
    an operation shaft inserted into the first hole and into the second hole, the operation shaft comprising:
        a first protrusion configured to engage with the first engagement surface; and
        a second protrusion configured to engage with the second engagement surface,
    wherein when the operation shaft rotates in the first rotation direction, the first protrusion engages with the first engagement surface and the second protrusion does not engage with the second engagement surface,
    when the operation shaft rotates in the second rotation direction, the second protrusion engages with the second engagement surface and the first protrusion does not engage with the first engagement surface;
    the first protrusion has a first height from an outer surface of the operation shaft,
    the second protrusion has a second height from the outer surface of the operation shaft, and
    the first height and the second height are different.

2. The bending operation mechanism according to claim 1, wherein:
    the first cylindrical disk comprises a first projection;
    the second cylindrical disk comprises a second projection; and
    further comprising a stopper configured to prevent the first rotation of the first cylindrical disk in the first rotation direction when the first projection contacts the stopper, and to prevent the second rotation of the second cylindrical disk in the second rotation direction when the second projection contacts the stopper.

3. The bending operation mechanism according to claim 2, further comprising:
    an operation knob provided to the operation shaft, the operation knob configured to rotate the first cylindrical disk and the second cylindrical disk.

4. The bending operation mechanism according to claim 2, wherein
    the first projection provided on an outer circumferential surface of the first cylindrical disk,
    the second projection provided on an outer circumferential surface of the second cylindrical disk, and
    the stopper is provided on a rotation path of the first projection and a rotation path of the second projection.

5. The bending operation mechanism according to claim 1, wherein
    the first inner peripheral surface includes,
        a first circumferential surface having a first inner diameter, and
        a second circumferential surface having a second inner diameter that is larger than the first inner diameter,
    the first engagement surface is provided between the first circumferential surface and the second circumferential surface,
    the second inner peripheral surface includes,
        a third circumferential surface having a third inner diameter, and
        a fourth circumferential surface having a fourth inner diameter that is larger than the third inner diameter,
    the second engagement surface is provided between the third circumferential surface and the fourth circumferential surface.

6. The bending operation mechanism according to claim 5, wherein
    when the operation shaft is configured to rotate in the second rotation direction, the first protrusion is configured to rotate within the second circumferential surface so as to be spaced apart from the first engagement surface, and
    when the operation shaft is configured to rotate in the first rotation direction, the second protrusion is configured to rotate within the fourth circumferential surface so as to be spaced apart from the second engagement surface.

7. The bending operation mechanism according to claim 5, wherein
    the second circumferential surface is provided larger than the first circumferential surface in a circumferential direction of the operation shaft, and
    the fourth circumferential surface is provided larger than the third circumferential surface in the circumferential direction.

8. The bending operation mechanism according to claim 1, further comprising:
    a first elastic body configured to bias the first cylindrical disk in the second rotation direction; and
    a second elastic body configured to bias the second cylindrical disk in the first rotation direction.

9. The bending operation mechanism according to claim 8, wherein
the first elastic body comprises a first spring; and
the second elastic body comprises a second spring.

10. The bending operation mechanism according to claim 9, wherein
the first spring comprises a first torsion spring; and
the second spring comprises a second torsion spring.

11. The bending operation mechanism according to claim 1, wherein a first center axis of the first cylindrical disk is coaxial with the second center axis of the second cylindrical disk.

12. The bending operation mechanism according to claim 1, further comprising the first wire and the second wire configured to bend a bending portion of the endoscope.

13. The bending operation mechanism according to claim 10, wherein
the first wire including the first proximal end portion connected to the first cylindrical disk, the first proximal end portion provided proximally relative to a first center axis of the first cylindrical disk when the operation shaft doesn't rotate in the first rotation direction and doesn't rotate in the second rotation direction; and
the second wire including the second proximal end portion connected to the second cylindrical disk, the second proximal end portion provided proximally relative to a second center axis of the second cylindrical disk when the operation shaft doesn't rotate in the first rotation direction and doesn't rotate in the second rotation direction.

14. The bending operation mechanism according to claim 1, wherein the first protrusion and the second protrusion are provided at a same circumferential position in a circumferential direction of the operation shaft.

15. The bending operation mechanism according to claim 1, wherein an entirety of the first protrusion and an entirety of the second protrusion are separately formed in a longitudinal direction of the operation shaft.

16. The bending operation mechanism according to claim 1, wherein the operation shaft has an obstruction provided on the outer surface of the operation shaft, the obstruction configured to prevent longitudinal movement of an adjacent one of the first cylindrical disk or the second cylindrical disk.

17. The bending operation mechanism according to claim 16, wherein the obstruction comprises a flange protruding from the outer surface of the operation shaft over an entire circumference of the shaft.

18. The bending operation mechanism according to claim 1, wherein the first cylindrical disk comprises a first pulley and the second cylindrical disk comprises a second pulley.

19. The bending operation mechanism according to claim 1, wherein the operation shaft comprises a surface provided between the first protrusion and the second protrusion, the surface has a third height, the third height is smaller than the first height and the third height is smaller than the second height.

20. An endoscope comprising the bending operation mechanism according to claim 1.

* * * * *